(12) United States Patent
Broas

(10) Patent No.: US 6,771,174 B2
(45) Date of Patent: Aug. 3, 2004

(54) DIGITAL PILLBOX

(75) Inventor: Edmundo R. Broas, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/769,153

(22) Filed: Jan. 24, 2001

(65) Prior Publication Data

US 2002/0097156 A1 Jul. 25, 2002

(51) Int. Cl.[7] .............................................. G08B 23/00
(52) U.S. Cl. ........................ 340/573.1; 340/309.15; 221/15; 368/10; 702/177; 705/3
(58) Field of Search ........................ 340/573.1, 309.15, 340/666; 221/2, 3, 15, 78; 368/10, 12, 108, 109; 702/177; 700/231; 705/2, 3; 600/300; 128/920, 921, 925

(56) References Cited

U.S. PATENT DOCUMENTS

| | | | | |
|---|---|---|---|---|
| 5,088,056 A | * | 2/1992 | McIntosh et al. | ............. 368/10 |
| 5,412,372 A | * | 5/1995 | Parkhurst et al. | ........... 340/568 |
| 5,646,912 A | * | 7/1997 | Cousin | ......................... 368/10 |
| 6,221,010 B1 | * | 4/2001 | Lucas | ......................... 600/300 |
| 6,259,654 B1 | * | 7/2001 | de la Huerga | ................ 368/10 |
| 6,294,999 B1 | * | 9/2001 | Yarin et al. | ............. 340/573.1 |
| 6,578,003 B1 | * | 6/2003 | Camarda et al. | ............... 705/3 |

OTHER PUBLICATIONS

Med–eMonitorTM System and Midi–Monitor by InforMedix Inc. Profile (Feed–back.com).*
Company Fact Sheet of Infor Medix, Inc. May 2003 (www.informedix.com).*

* cited by examiner

*Primary Examiner*—Davetta W. Goins
(74) *Attorney, Agent, or Firm*—Trop, Pruner & Hu, P.C.

(57) ABSTRACT

A digital pillbox, a personal alert device, and a computer-implemented system and method for aiding a patient in maintaining a desirable dosage schedule of medicines. Sensors and logic determine a time and quantity of a dosage taken, if any, and the system keeps records and monitors against a schedule and against a dynamic, learning, behavioral model of the patient. The schedule is remotely updateable by e.g. the patient's pharmacist. The system is equipped to alert e.g. a friend of the patient, or emergency services, if the patient fails to take the desired medications or if the patient's dosage behavior exhibits a significant change.

43 Claims, 3 Drawing Sheets

DIGITAL PILLBOX

BACKGROUND OF THE INVENTION

1. Technical Field of the Invention

The present invention relates generally to monitoring a patient's consumption of medication, and more specifically to an apparatus and computer-implemented method for such.

2. Background Art

Medication delivery and monitoring systems typically rely heavily upon human attention and human action. If a patient fails to take prescribed medication, or to take it in a timely manner, it might be that nobody notices, including the patient herself. If the patient's supply of a particular medication has, or is about to, run out, it may again be that nobody notices. Some patients are required to take a large number of medications, each perhaps having a unique dosage schedule. Patients frequently make mistakes in calculating the timing and/or quantity of medications. Except in very narrowly defined circumstances, there is no automated or computed delivery mechanism to ensure that patients receive medications properly. One such limited example is the electrically-controlled plunger mechanism which hospitals employ to deliver painkillers or other single, liquid medications at a predetermined, constant rate. But that mechanism is not suitable for delivering multiple medications, nor medications which come in non-liquid form.

BRIEF DESCRIPTION OF THE DRAWINGS

The invention will be understood more fully from the detailed description given below and from the accompanying drawings of embodiments of the invention which, however, should not be taken to limit the invention to the specific embodiments described, but are for explanation and understanding only.

DETAILED DESCRIPTION

Figure 1:
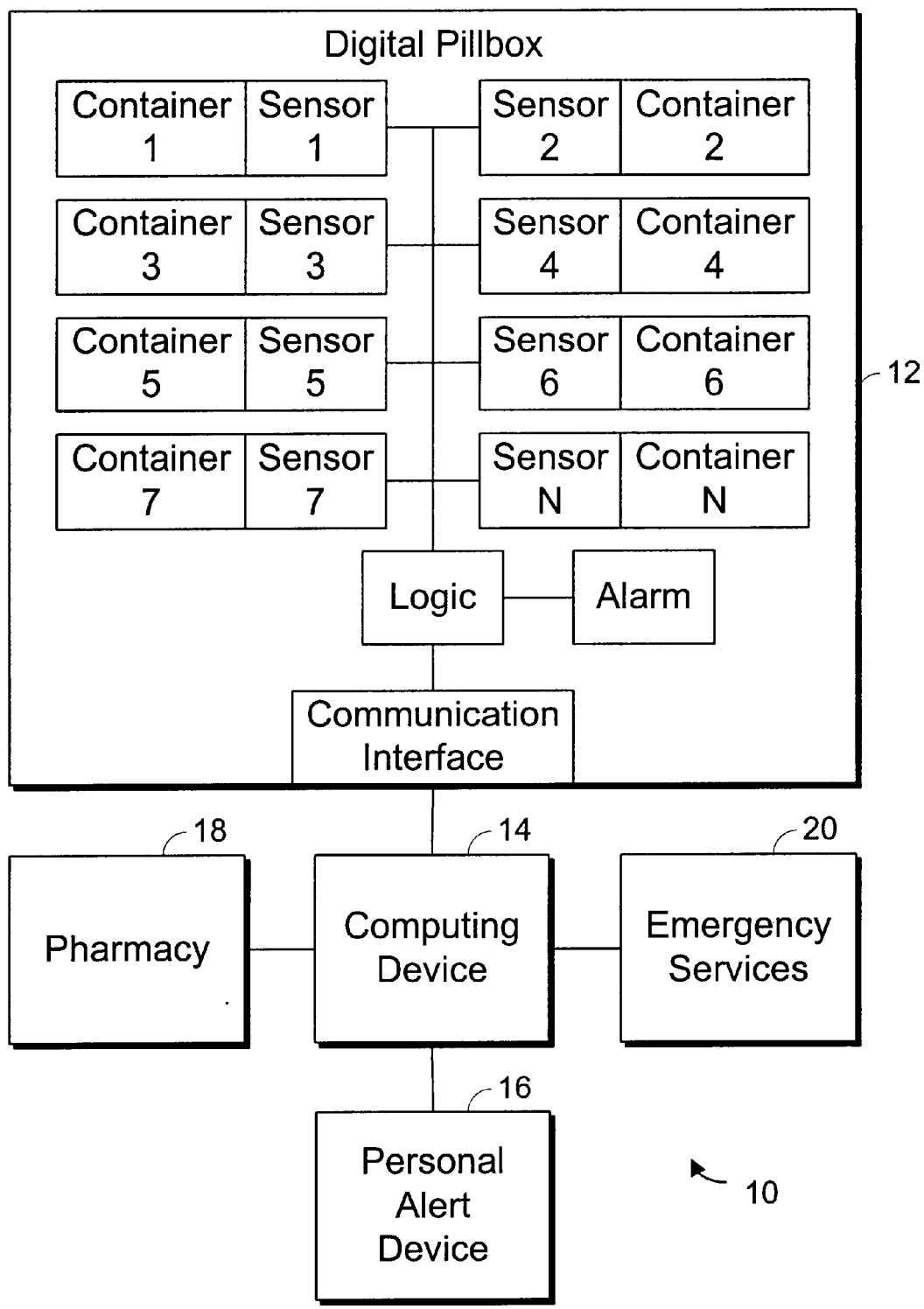
FIG. 1 shows a system according to one embodiment of this invention, highlighting a digital pillbox of the system.

FIG. 1 illustrates one exemplary embodiment of a system 10 utilizing this invention. The system includes a digital pillbox 12 which can communicate with a computing device 14. The computing device can, optionally, communicate with a personal alert device 16, a pharmacy 18, and/or emergency services.

The digital pillbox includes one or more containers (Container 1-N) which have one or more corresponding sensors (Sensors 1-N) which are adapted to determine a quantity of medication in their respective containers. In one embodiment, the sensors measure weight. In other embodiments, the sensors may measure some other characteristic such as volume, or they may be adapted for e.g. computer vision to detect the medication. The invention may be used with other than medication, but will be described with respect to medication for purposes of illustration. In some embodiments, the containers may not be an integral part of the digital pillbox. The digital pillbox may, in some embodiments, incorporate logic for performing various functions such as calibrating the sensors or for operating the communication interface to the computing device. In various embodiments, the functionalities of the digital pillbox and the computing device may be distributed between them differently than described herein, without departing from the principles of this invention. In some embodiments, the digital pillbox may further include an alarm for alerting the patient that, for example, it is time to take a medication, or that a medication is nearly gone, or the like. The logic of the digital pillbox may be constituted in hardware, software, firmware, a combination, or other suitable means.

The computing device may be embodied as a personal computer, an appliance, a dedicated device, or any suitable form, and may be implemented using hardware, software, firmware, a combination, or any suitable means.

The personal alert device may be, in one embodiment, an RF receiver bracelet or key chain. In other embodiments, it may be some other form. In many embodiments, the personal alert device will be suitable for wearing on or carrying by the patient, to enable the computing device to deliver alerts to the patient. In other embodiments, it may be, for example, a remote device suitable for placing on a bedside table, or the like. In many embodiments of the system, the personal alert device may be optional or omitted entirely, such as where the alerts are delivered solely through the computing device itself and/or the digital pillbox.

The pharmacy 18 may constitute any sort of communication mechanism at a pharmacy. In one desirable embodiment, the pharmacy 18 represents a computing platform operated by the patient's pharmacy and including therein a database of medication data pertaining to the patient and her medications. In other embodiments, the pharmacy 18 may simply represent a telephone or fax machine or other such data delivery apparatus located at the patient's pharmacy. It is, of course, not strictly necessary that it be an actual pharmacy, even though it is being explained here as a pharmacy. It could alternatively be a doctor's office or other such entity having or needing information about this patient and her medications.

Similarly, the emergency services 20 may constitute a computing platform, telephone, fax machine, or other data delivery mechanism, and may represent 9-1-1 or even a friend or relative of the patient.

The computing device may communicate with each of the digital pillbox, the personal alert device, the pharmacy, and the emergency services unidirectionally in some embodiments, and bidirectionally in others. The link between them may be any mechanism suitable for the application at hand. For example, in some embodiments, the link may be wired or wireless, radio frequency, laser, optical, infrared, Ethernet, USB, Firewire, serial, parallel, cellular, home wiring based, and so forth. The data transmitted to and/or from the computing device and the other entities may constitute digital data, digitized or synthesized or recorded audio data, or any other suitable data delivery form.

Figure 2:
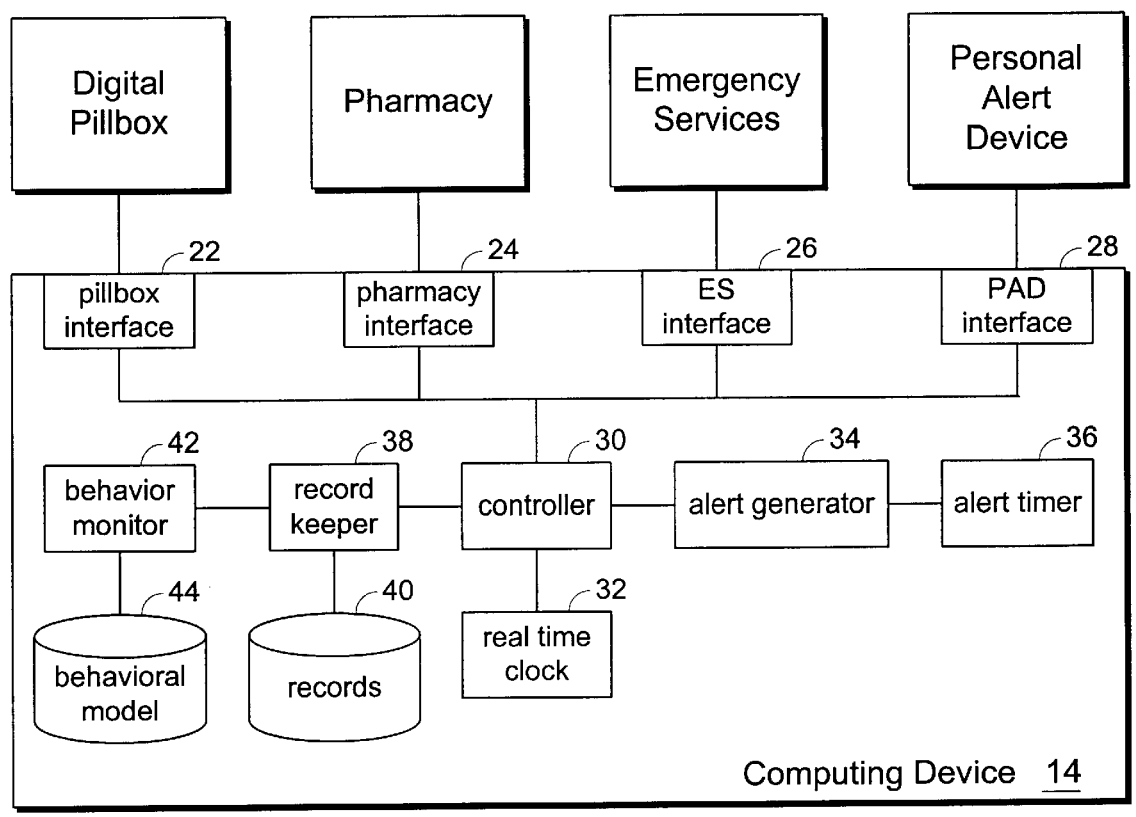
FIG. 2 shows one embodiment of an exemplary computing device such as may be used in the system of FIG. 1.

FIG. 2 illustrates one embodiment of the system 10 utilizing this invention, with more detail shown regarding the computing device 14. The computing device includes one or more interfaces to the various other entities with which it can communicate, including a pillbox interface 22, a pharmacy interface 24, an emergency services interface 26, and a personal alert device interface 28. In various embodiments, certain ones of these interfaces may be combined as a single interface. In various embodiments, certain ones of these interfaces may utilize the same communication technology. In one embodiment, the digital pillbox interface is a USB interface, the pharmacy and emergency services interfaces use the regular telephone system, and the personal alert device interface uses RF.

The computing device further includes a controller 30 which performs many of the functionalities of the computing device. In some embodiments, the controller may comprise a microprocessor and one or more programs for it. In other embodiments, the controller may comprise hard-wired logic, or other suitable means. The computing device includes a real-time clock 32 which is coupled to the controller and which is used in performing time-based calculations. The real-time clock may be a stand-alone semiconductor device, or it may simply be software running on the controller, or it may include a radio receiver to receive a time broadcast such as from a centralized or atomic clock, or other suitable means.

The computing device also includes an alert generator 34 coupled to the controller, and an alert timer 36 coupled to the alert generator. The alert generator and alert timer may be separate devices or they may be constructed as one unitary device. Alternatively, they could be implemented as additional programming of the controller, or in other suitable ways. The alert timer is used in performing calculations used in generating and sending alerts.

The computing device further includes a record keeper 38 which has storage for records 40 regarding the patient and medications. The record keeper may be implemented in hardware, software, or a combination. The storage may include a hard disk, optical disc, semiconductor memory device, or other suitable storage mechanism. The record keeper may be autonomous, or it may be implemented as, for example, one or more programs to be executed on the microprocessor of the controller.

The computing device further includes a behavior monitor 42 which has storage for a behavioral model 44 which is used in monitoring the medication-taking behavior of the patient. The behavioral model may be implemented as a database, an expert system, using artificial intelligence techniques, or any other suitable means.

Figure 3:
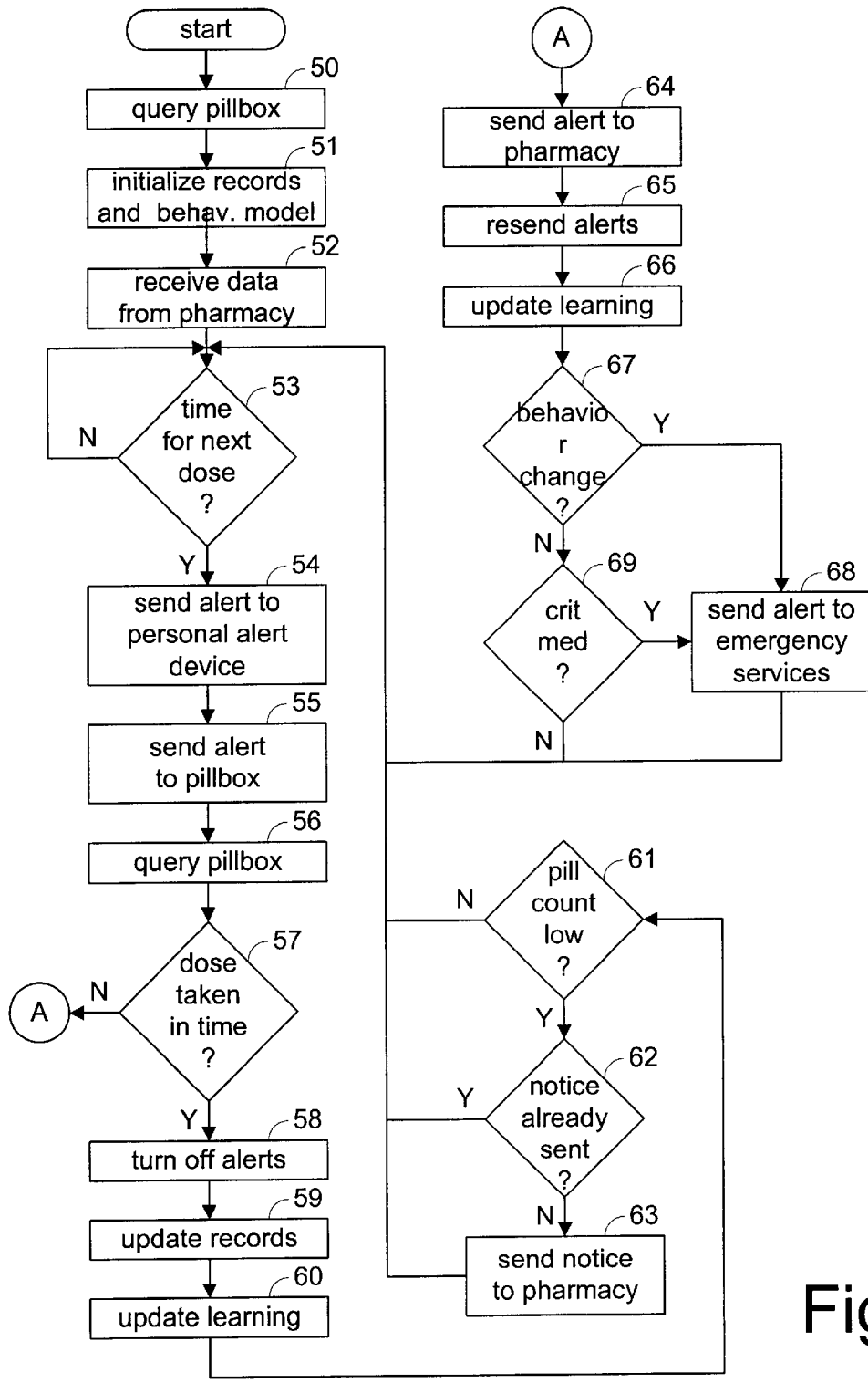
FIG. 3 shows one exemplary embodiment of a method of operating the computing device.

FIG. 3 illustrates one exemplary method of operation of the computing device. The reader should continue to refer also to FIGS. 1 and 2. The skilled reader will readily appreciate that this is only one example of a multitude of suitable methods, and that various changes, omissions, modifications, and additions may be made to the illustrated method without departing from the scope of the invention.

The method begins with the computing device querying (50) the pillbox to, for example, gather a starting point for initializing (51) the records of the record keeper. The controller may query the digital pillbox's logic to determine the quantity of medication in each of the containers. This may, in some modes, include establishing a baseline or zero setting for each, which may later be used in determining whether the container is empty. In one mode, the computing device may prompt the patient to place the empty containers on their sensors and, for example, press a key. In other modes, the empty weight may be pre-programmed, especially in those embodiments in which the containers are an integral part of the digital pillbox. This may further include the sensors re-measuring the containers after the patient fills the containers with the respective medications. The controller can then relay this information to the record keeper for initialization of the records in storage. In some instances, such as upon first usage by a new patient, the controller may also trigger the behavior monitor to initialize the behavioral model for this patient.

The computing device may receive (52) data from the pharmacy identifying the medications, in which containers they should be placed, their dosage schedule, the patient, and so forth. Alternatively, the patient could manually enter this information. This information is stored in the record storage by the record keeper. In one embodiment, the pharmacy may program the records with information specifying how much each dosage weighs. In another embodiment, the patient may train the records by adding or subtracting a specified number of dosages, with the logic and/or controller doing the math on the before and after weight. Other methods will be appreciated by the skilled reader who is armed with this disclosure.

The computing device's alert timer waits (53) for a next dosage time, and at the appointed time, the alert generator sends (54) an alert to the personal alert device if one is in use, and sends (55) an alert to the digital pillbox if the digital pillbox is equipped with an alarm device. In some embodiments, the alerts may include data such as text or synthesized speech indicating "3:30 pm, take 100 mg (two tablets) of thorazine from container 4" or the like. In other embodiments, the alerts may simply be a voltage level that activates the alarm device. Any suitable alert system may be employed, independently, for the personal alert device and for the digital pillbox.

The computing device queries (56) the digital pillbox to determine whether (57) the medication has been taken within a period of time specified by the record keeper. The sensors, together with the digital pillbox's logic and the computing device's controller and records, may combine to determine how much medication was taken from which containers.

If the correct dosage of the correct medication was taken within the allotted time window, the computing device may turn off (58) the alarms of the digital pillbox and the personal alert device (in embodiments where those need turning off). The record keeper updates (59) the records, and the behavior monitor updates (60) the learning in the behavioral model.

The behavioral model may, in one embodiment, be set up to watch for changes in behavior. For example, if the patient has, in the past, consistently taken her heart medication within ten minutes of being notified by the personal alert device, but suddenly starts waiting an hour or more before taking it, this may indicate some cognitive or other problem which may warrant intervention by emergency services, the patient's friends or family, a hospice aide, or the like. The skilled reader will appreciate the variety of possibilities for such a behavioral model.

The record keeper determines (61) whether any of the medications are running low. It may advantageously utilize a pre-programmed or a trained zero baseline measure for the empty containers. If a medication is running low, and if (62) the computing device has not already sent notification to the pharmacy, it now sends (63) notification. The notification may take any suitable form. In one embodiment, a text or fax message is sent, for example saying "Patient Henrietta James ID number 12348765 has only three days' worth of AZT left." As another example, the computing device could place a voice synthesized phone call to the pharmacy. The parameters controlling the sending of such an alert may vary from patient to patient, from medication to medication, and so forth. They may be pre-programmed in the computing device, or they may be downloaded from the pharmacy, or other suitable means for establishing them.

The system then returns to waiting for the next medication time.

If (57), however, the patient failed to take her medication within the appointed window of time, or if the patient has taken the wrong medication, or the wrong amount of medication, the computing device sends (64) an alert to the pharmacy. This alert may, again, take any suitable form. The computing device may resend (65) the alerts to the personal alert device and the digital pillbox. The behavior monitor may update (66) the behavioral model as appropriate.

If (67) the behavioral model identifies a behavioral change that meets predetermined criteria in the model, the computing device sends (68) an alert to emergency services, a pre-specified friend or neighbor, a doctor, or the like. The skilled reader will appreciate that various criteria may be defined, taking into account characteristics of the medication, of the type or extent of the behavioral change, or even of the patient's status such as age or infirmity. In some embodiments, the behavioral model may exhibit adaptive learning. In others, it may simply apply predetermined rules such as if (69) the medication which has been missed is of a critical nature, such as a cancer treatment or a heart medication, the alert should be sent immediately, without waiting to see if any long-term behavioral change is exhibited. The computing device then returns to wait for a next medication time.

While FIG. 3 has been explained as illustrating a method of operation of the invention, it may also be interpreted as representing a computer-accessible delivery mechanism in which is embodied instructions, routines, programs, control codes, interpretive language, firmware, or the like which, when accessed by a machine, cause the machine to perform the method as explained above. In one embodiment, this delivery mechanism may be a recordable medium such as a CD-ROM, tape, flash memory device, DVD, removable hard drive, floppy disk, or the like. In another embodiment, it may be a communication means such as the internet, a LAN, a cellular network, or other such means, in which such instructions etc. are represented as voltage levels, data packets, or the like.

In the interest of clarity and simplicity, the invention has been described in terms of a single patient. However, the skilled reader will appreciate that the invention may readily be employed in monitoring a plurality of patients. Similarly, the invention has been described in terms of a system having a single digital pillbox, a single personal alert device, a single pharmacy, and a single emergency service provider, but the skilled reader will appreciate that the invention may be implemented to support a plurality of any or all of those, either in conjunction with a single computing device or a plurality of computing devices. The skilled reader will further appreciate that various of the functionalities described herein may in some embodiments be practiced at different locations or upon different hardware than that disclosed herein. As but one example, the records database and/or the behavioral model might be implemented at the pharmacy rather than at the patient's location, without departing from the scope of this invention.

Reference in the specification to "an embodiment," "one embodiment," "some embodiments," or "other embodiments" means that a particular feature, structure, or characteristic described in connection with the embodiments is included in at least some embodiments, but not necessarily all embodiments, of the invention. The various appearances "an embodiment," "one embodiment," or "some embodiments" are not necessarily all referring to the same embodiments.

If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Those skilled in the art having the benefit of this disclosure will appreciate that many other variations from the foregoing description and drawings may be made within the scope of the present invention. Indeed, the invention is not limited to the details described above. Rather, it is the following claims including any amendments thereto that define the scope of the invention.

What is claimed is:

1. An apparatus comprising:

logic;

a communication interface coupled to the logic;

at least one sensor coupled to the logic;

at least one medicine container, each coupled to a respective one of the at least one sensors; and a computing device coupled to the communication interface via a communication link, the computing device including data storage for a behavioral model to track a patient's medicine-taking behavior, said behavioral model being capable of adaptive learning, and an alert signal generator to send alert signals if changes in medicine-taking behavior data in the behavioral model meet predetermined criteria in the behavioral model.

2. The apparatus of claim of claim 1 wherein:

the at least one sensor comprises at least one weight-based measuring apparatus.

3. The apparatus of claim 1 wherein:

the at least one sensor comprises a plurality of sensors; and the at least one medicine container comprises a plurality of medicine containers.

4. The apparatus of claim 3 wherein:

the plurality of sensors comprises a plurality of weight-based measuring mechanisms.

5. The apparatus of claim 1 further comprising:

an alarm.

6. An apparatus comprising:

processing means for performing operations;

means, coupled to the processing means, for generating alerts;

means, coupled to the processing means, for keeping records including information indicating medicine dosages; and means, coupled to the means for keeping records, for modeling behavior of a patient based upon the information indicating medicine dosages, in which the means for modeling behavior is adapted to identify a change in the patient's medicine-taking behavior, exhibit adaptive learning and generate an alert signal if the changes meet predetermined criteria in the model.

7. The apparatus of claim 6 further comprising:

an alert generator coupled to the processing means.

8. The apparatus of claim 6 further comprising:

an interface for coupling the apparatus to a pillbox.

9. The apparatus of claim 8 further comprising:

the pillbox.

10. The apparatus of claim 9 wherein the pillbox comprises:

at least one sensor for measuring a quantity of medicine.

11. The apparatus of claim 10 wherein the at least one sensor comprises:

a plurality of sensors.

12. The apparatus of claim 10 wherein the pillbox further comprises:

a plurality of containers for holding medicines.

13. The apparatus of claim 6 further comprising:

a personal alert device; and an interface for the apparatus to communicate with the personal alert device.

14. The apparatus of claim 13 further comprising:

a digital pillbox having a plurality of sensors for measuring quantities of medicines; and an interface for the apparatus to communicate with the digital pillbox.

15. A method comprising:

receiving data indicating a measurement of a medication in a container;

comparing the received data to previously-received data to generate a difference;

responsive to the difference, calculating an amount of the medication removed from the container;

maintaining data for a behavioral model of a patient's medicine dosage history, said behavioral model adapted to exhibit adaptive learning; and generating an alert signal if changes in the patient's medicine dosage history meet predetermined criteria in the behavioral model.

16. The method of claim 15 further comprising:

determining a time at which the medication was removed from the container; and determining whether the time is within a predetermined guideline for a dose of the medication.

17. The method of claim 16 further comprising:

if the time is not within the predetermined guideline, sending an alert to an external entity.

18. The method of claim 16 wherein the external entity is an emergency services provider.

19. The method of claim 15 further comprising:

sending an alert to trigger an alarm alerting a patient that it is time to take the medication.

20. The method of claim 19 wherein sending the alert comprises:

sending the alert to a digital pillbox.

21. The method of claim 19 wherein sending the alert comprises:

sending the alert to a personal alert device.

22. The method of claim 19 further comprising:

detecting that the medication has been removed from the container;

determining that the removal was within a predetermined time for a patient to take a dosage of the medication; and responsive thereto turning off the alarm.

23. The method of claim 22 further comprising:

updating a record.

24. The method of claim 23 further comprising:

updating learning in the behavioral model.

25. The method of claim 15 further comprising:

receiving medical information from a pharmacy.

26. A method comprising:

determining a time at which a patient takes a dosage of a medication;

updating data in a behavioral model in response to the determining of the time, the behavioral model modeling the behavior of the patient taking the medicine;

sending an alert signal if changes in the time at which the patient takes a dosage meet predetermined criteria in the behavioral model; and adaptively learning by the behavioral model.

27. The method of claim 26 wherein the determining comprises:

acquiring data from a sensor coupled to a container containing the medication.

28. The method of claim 27 wherein the acquiring data comprises:

the sensor weighing the container and medication in the container.

29. The method of claim 27 further comprising:

acquiring data from a plurality of sensors each coupled to a respective container of a plurality of containers containing a plurality of medications.

30. The method of claim 26 wherein the determining comprises:

recording a first indication of a first amount of medication in the container;

recording a second indication of a second amount of medication in the container;

comparing the first indication to the second indication to generate a difference amount; and comparing the difference amount to a predetermined amount of a proper dosage.

31. The method of claim 30 further comprising:

generating the first and second indications by weighing the container and medication.

32. The method of claim 30 further comprising:

waiting for a time at which the patient is supposed to take a next dosage of the medication.

33. A machine-accessible delivery mechanism comprising:

instructions which, when executed by a machine, cause the machine to execute the method of claim 15.

34. The machine-accessible delivery mechanism of claim 33 further comprising:

instructions which, when executed by the machine, cause the machine to further execute the method of claim 16.

35. A machine-accessible delivery mechanism comprising:

instructions which, when executed by a machine, cause the machine to execute the method of claim 26.

36. The machine-accessible delivery mechanism of claim 35 further comprising instructions which, when executed by a machine, cause the machine to execute the method of claim 29.

37. The machine-accessible delivery mechanism of claim 31 further comprising:

instructions which, when executed by a machine, cause the machine to execute the method of claim 30.

38. The apparatus of claim 6 wherein the change in the patient's medicine-taking behavior comprises a change in at least one of:

timeliness; and dosage.

39. The method of claim 15 wherein the maintaining the behavioral model comprises:

detecting that the patient's timeliness in taking a current dosage of medicine indicates a behavioral change versus a behavioral history of the patient.

40. The apparatus of claim 6 wherein the change in the patient's medicine-taking behavior comprises:

a change in the patient's medicine-taking behavior if alerted one or more times to take a particular dose of medicine.

41. The method of claim 26 further comprising:

alerting the patient one or more times to take a particular dose of medicine, and updating the data in the behavioral model in response to the alerting of the patient.

42. A method comprising:

monitoring a patient's response to one or more alerts to take a particular dose of medicine;

determining if the patient's response to the one or more alerts has changed, said determination based on a behavioral model of the behavior of the patient taking the medicine; and alerting a third party if changes in the patient's response meet predetermined criteria in the behavioral model.

43. The method of claim 42 further including exhibiting adaptive learning in the behavioral model.

* * * * *